(12) United States Patent
Ternström (10) Patent No.: US 6,432,111 B1
(45) Date of Patent: *Aug. 13, 2002

(54) DEVICE FOR EXTRACTION OF TISSUE OR THE LIKE (75) Inventor: Staffan Ternström, Varberg (SE)

(73) Assignee: Safe Conduct AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,155

(22) Filed: Oct. 17, 2000

Related U.S. Application Data (62) Division of application No. 09/155,253, filed on Sep. 22, 1998, now Pat. No. 6,152,932.

(30) Foreign Application Priority Data

Mar. 25, 1996 (SE) ................................................ 9601122
Feb. 12, 1997 (WO) ................................. PCT/SE97/00210

(51) Int. Cl.<sup>7</sup> .......................... A61B 17/24; A61B 17/26
(52) U.S. Cl. ........................ 606/114; 606/113; 606/127
(58) Field of Search ................................ 604/104–107, 604/96.01, 114; 606/190, 191, 198, 110, 114, 127, 128, 113; 600/564–566

(56) References Cited

U.S. PATENT DOCUMENTS 5,034,001 A * 7/1991 Garrison et al. ............... 604/53
5,074,871 A * 12/1991 Groshong et al. ........... 606/170
5,197,968 A * 3/1993 Clement ...................... 606/115

* cited by examiner

Primary Examiner—Brian L. Casler
Assistant Examiner—Jennifer Maynard
(74) Attorney, Agent, or Firm—Orum & Roth (57) ABSTRACT The present invention relates to a surgical instrument to be used in certain endoscopic surgical operations, such as laparoscopic surgery, in order to fix, enclose, and extract a specimen, such as an organ or tissue. The device in accordance with the invention comprises a shank part and an entrapment part mounted on one end of the shank part. The characteristic features of the invention are that the entrapment part is provided with at least one opening for insertion of the specimen, such as an organ or tissue, said opening being expandable to an open condition and contractible to an at least partly closed condition, and in that assumes a fusiform configuration, at least when the opening is in its closed condition.

15 Claims, 10 Drawing Sheets

DEVICE FOR EXTRACTION OF TISSUE OR THE LIKE

This application is a division of U.S. application Ser. No. 09/155,253, filed Sep. 22, 1998, now U.S. Pat. No. 6,152,932.

TECHNICAL FIELD

The present invention relates to a surgical instrument to be used in certain endoscopic surgical operations, such as in laparoscopic surgery, in order to extract a specimen, such as an organ or tissue.

BACKGROUND

Laparoscopic surgery, also known as keyhole surgery, has gained increasing importance within general surgery and gynaecological surgery. The advantages obtained compared with conventional surgery are considerable to the patient and society alike. In laparoscopic surgery small puncture orifices are made in the abdominal wall through which trocars (tubular sleeves) are inserted, said trocars serving as a means for introduction of the laparoscopic instrument as well as one or several working instruments. The abdomen is inflated by gas, which increases the abdominal volume considerably, allowing survey and accessibility. The image of the surgical area is transmitted to a monitor and the disordered organ is isolated and separated from surrounding tissue with the aid of the operational instrument. The surgical technique, instrument and other equipment used for this purpose are well known and highly developed. The specimen (organ, surgically removed tissue) is then to be removed from the abdomen. When the specimen is small-sized it may be extracted through a trocar directly but when the specimen is large it is either necessary to open the abdomen by making an incision therein (thus reducing the advantages gained by the laparoscopic surgical operation) or to fragmentize (morcellate) the specimen. Instruments for this purpose (morcellaters) have been known for several decades (for example the instrument known as Serrated edge Macro Morcellator "SEMM" manufactured by Wisarp in Germany) and in recent years several models have been developed. A morcellator of this kind is described for instance in U.S. Pat. No. 5,443,472 comprising two rods which are carried down into the abdomen and one of which comprises a net which may be gathered together and which is positioned in such a manner as to extend around the other rod and the specimen. The second rod comprises an outer tube having an opening therein and an inner tube having a cutting edge. When the net is gathered together a part of the specimen is forced to enter through the opening, whereupon the inner tube is forced downwards and cuts off the protruding part of the specimen, the inner tube is withdrawn, and the procedure may be repeated.

The problem connected with this and other morcellators are, however, considerable. This is due essentially to the fact that the specimen, such as an organ or tissue, at best is only partly enclosed by a retaining device;
consequently the specimen is insufficiently fixed;
reconstruction of the specimen after morcellation is not possible; and
there is no safe barrier between the morcellator and the abdomen.

The consequences are several:

1. The fragments of the specimen, such as an organ or tissue, cannot be cut from the specimen in a planned and optimum manner.
2. The morcellation is a lengthy operation, or cannot be carried out at all if the specimen is very large.
3. In the finishing phase the specimen is cut through from several directions and consequently limp and difficult to handle.
4. It may be difficult, even impossible, for the pathologist to correctly assess the specimen microscopically, since the specimen is presented to him in fragments that cannot be orientated relative to one another, and one consequence thereof is that the laparoscopic surgical technique is unsuitable for example for certain types of cancer surgery.
5. Damage may be made to surrounding organs (for example intestines and blood vessels) during the morcellation since there is no safe barrier between on the one hand the morcellator and the specimen and on the other the abdominal cavity.
6. Waste from the specimen may contaminate the abdominal cavity or the abdominal wall (infected specimen, cancer cells).

Also when the specimen, such as an organ or tissue, is small and should not need to be fragmentized extraction thereof could nonetheless be difficult using prior art equipment. Prior art equipment often comprises a bag or sack of some kind which is introduced into the abdomen through the trocar. When the specimen is entrapped and the equipment is pulled upwards it may, however, be deformed in an unfavourable manner or assume an oblique position, making it impossible to extract it through the trocar.

These and other problems are complicating features of the laparoscopic surgery and restrict its use and application. Under corresponding conditions the above is applicable also to the operative thorascopy (keyhole surgery in the thoracic cavity).

OBJECT OF THE INVENTION

The object of the present invention is to provide a device to be used in endoscopic surgical operations in order to extract a specimen, such as an organ or tissue, which device wholly or completely obviates the above-mentioned problems connected with the prior art technology. This object is achieved by means of a device as defined in claim 1.

DESCRIPTION OF PREFERRED EMBODIMENTS

The device in accordance with the invention will be described in more detail in the following by way of embodiments and with reference to the accompanying drawings.

Figure 1:
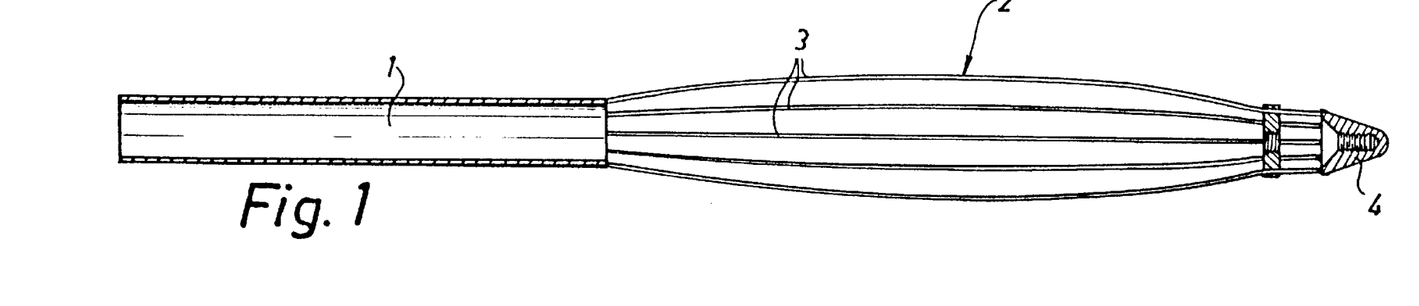
FIG. 1 is a cross-sectional view of a part of a device in accordance with the invention.
Figure 2:
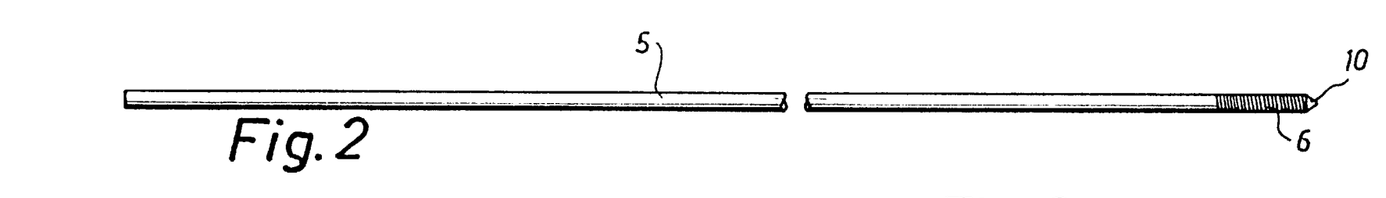
FIG. 2 shows a manipulating rod to be used together with the device of FIG. 1.
Figure 3:
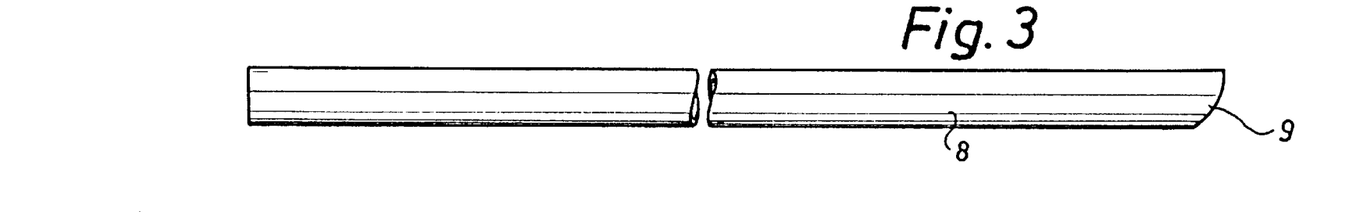
FIG. 3 shows an inner tube having a cutting edge, to be used together with the device of FIG. 1.

FIGS. 1–3 illustrate a device in accordance with the invention. As appears from FIG. 1 the device comprises a shank part 1 and an entrapment part 2. In this case, the shank part consists of a tube and the entrapment part of an expandable basket member. The expandable basket member consists of elastically resilient wires 3 extending from the lower or distal end of the tube to a round lower or distal bottom member 4. The wires, which could be made from e.g. spring steel, in this case essentially extend in planes including the prolongation of the shank centre axis. However, it is likewise possible to arrange the wires in such a manner that instead they may also turn about the centre axis.

Preferably, the wires are positioned symmetrically about the centre axis of the device.

On its face turned towards the basket 2 the bottom member 4 is provided with a threaded bore. The manipulating rod 5, which is illustrated in FIG. 2, may, when having been carried through the upper tube 1 be screwed to the bottom member 4 owing to the rod being correspondingly threaded at least at its distal end 6. Other ways of attaching the manipulating rod 5 to the bottom member are of course possible, for instance by means of a bayonet coupling. In addition, the manipulating rod 5 is of sufficient length to allow it to be fastened to and removed from the bottom member 4 by manipulation of the rod externally of the shank part when inserted through the latter, and preferably the rod has a comparatively pointed front or distal end 10. As illustrated in FIG. 2, the manipulating rod 5 may be completely straight but at least the lower part thereof may be slightly curved in order to increase the space inside the basket, and/or it may be made from a resiliently flexible material.

A sliding disc 7 is arranged above the bottom member and also the disc has a threaded bore or corresponding means to allow it to be attached to the manipulating rod 5. At its outer periphery the sliding disc 7 is provided with perforations through which extend the wires of the basket.

When the manipulating rod 5 has been passed through the shank 1 and is about to be secured by screw engagement, it is, in a first position, secured only to the sliding disc 7 whereas in a second position it is secured to the bottom member 4. In its second position the rod could, however, be secured both to the bottom member 4 and to the sliding disc 7.

FIG. 3 illustrates an internal tube 8 the external diameter on which essentially coincides with or is slightly smaller than the inner diameter of the shank part 1. Consequently, the inner tube introduced into the shank part has a comparatively snug fit therein. In addition, the inner tube 8 is formed with a cutting edge 9 at one of its ends. The cutting edge could be replaceable, and could for instance be attached to the inner tube by screw engagement.

The side of the sliding disc 7 that is turned towards the shank preferably is formed with an internally essentially conical guide means (not shown) to facilitate introduction of the manipulating rod 5 into the threaded hole in the disc 7. The guide member may also serve as a back up means to the cutting edge 9. Preferably, the guide member is made from a comparatively soft material that does not damage the edge of the cutting edge 9.

In use, the basket 2 and parts of the shank 1 are first introduced into the abdominal cavity through the abdominal wall of She patient. The manipulating rod is then introduced and screwed to the bottom member 4. Upon retraction of the manipulating rod the basket 2 will expand, since the retraction movement forces the two fastening points of the wires closer to one another. In the expanded position the middle areas of the wires also are spaced further apart than is the case when the basket assumes its unexpanded position.

By means of an additional instrument (not shown) which has been introduced into the abdomen through an other puncture orifice through the abdominal wall, a specimen, such as an organ or tissue, may now be entered into the basket through one of the inter-wire gaps. The bottom member is then pushed backwards once more and the manipulating rod is unscrewed and extracted. In this position the resilient wires tend to return the basket to its original, unexpanded condition and in doing so they exert a radially inwardly directed Force on the specimen. It is now possible to position and orientate the latter, if needed, in a desired position inside the basket with the aid of suitable instruments which are introduced into the basket by way of the shank or by way of other (existing) orifices in the abdominal wall. Instruments for other purposes, such as for flushing and suction to evacuate liquid-laden parts of the specimen (cysts), obviously could also be introduced via the shank.

The manipulating rod could thereafter again be passed through the shank part, its pointed forwards end 10 penetrating the specimen, centring the latter, whereupon the rod is screwed to the sliding disc 7. Optionally, the manipulating rod may be hollow and formed with lateral apertures, allowing it to simultaneously serve as a rinsing/suction device.

Figure 4:
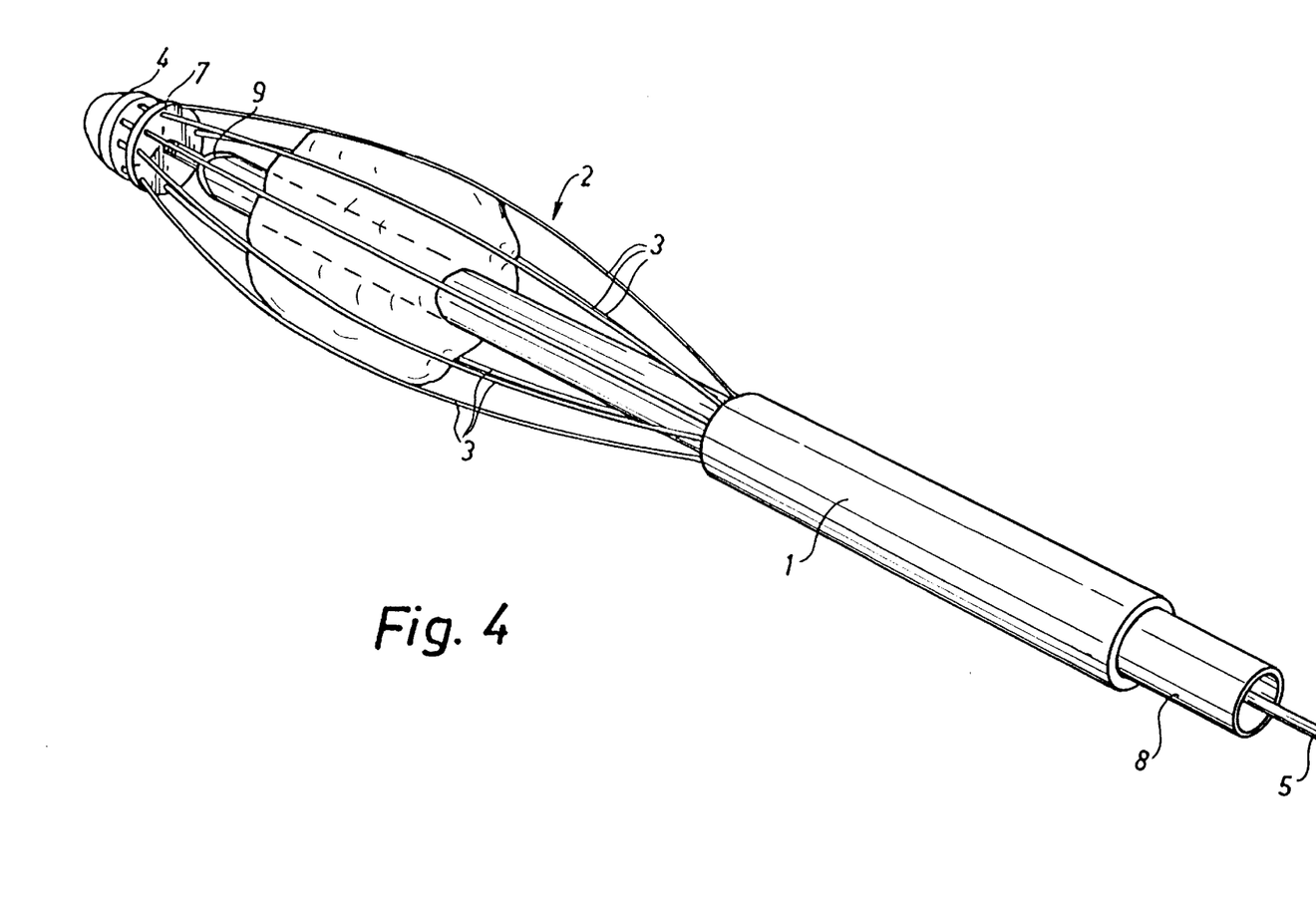
FIG. 4 is a perspective view of a device in accordance with the invention, a specimen, such as an organ or tissue, having been introduced into the device.

By pushing down the inner tube 8 through the shank part as illustrated in FIG. 4 and further down through the basket 2 to the vicinity of the sliding disc 7 the cutting edge 9 will cut out a central cylinder-shape piece of the specimen, such as an organ or tissue, inside the basket, and this specimen cylinder accompanies the inner tube as she latter is subsequently retracted. Advantageously, the tube 8 is forced through the specimen by means of a lever mechanism or the like departing from the parts of the shrank and the tube that are positioned externally of the abdomen. Such a mechanism or equivalent means may also serve to restrict the movability between the shank including the basket in which the specimen is fixed, and the inner tube, allowing movement in the axial direction only. Owing to this arrangement, the inner tube will move relative to the rest of the device in an identical manner each time and above all, without being rotated. Alternatively, the tube may, however, be affected by a rotating force or a guide so as to be rotated down through the specimen.

Figure 5:
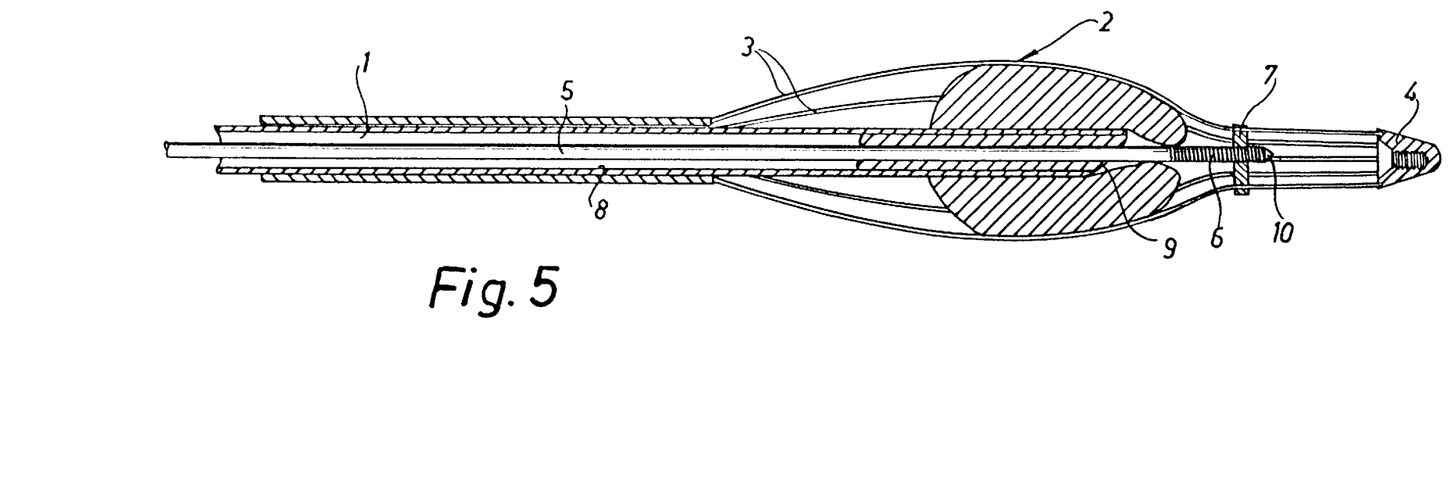
FIG. 5 is a cross-sectional view of a device in accordance with FIG. 4, showing a part of the specimen cut out, the sliding disc in a partly upper position and the inner tube being retracted.

Once the central cylinder of the specimen thus has been extracted, the basket compresses the cylindrical cavity formed in the specimen. Optionally, also the sliding disc 7 may be exposed to an axial force as illustrated in FIG. 5, displacing it along the wires towards the shank, which increases the radial force exerted by the basket inwards, towards the centre, and in addition forces the specimen upwards towards the shank part 1. The sliding disc 7 is thereafter retained in this partly upwardly pulled position and once again a central cylindrical piece is cut out of the specimen, such as an organ or tissue, by forcing the inner tube down through the latter, and the procedure is repeated in this manner until the specimen is completely or almost completely extracted, whereupon the device is removed from the patient. In this connection it is a highly beneficial feature that the last and limp piece of the specimen can be extracted by means of the device and does not need to be extracted separately.

Optionally, the cutting edge 9 when replaceable may be constructed as a cutting blade which is curved and somewhat overlapping and consequently resiliently expandable. Owing to this arrangement the circumference of the cutting edge will widen somewhat when being forced down through the specimen but be compressed by the internal restriction of the wire basket upon its approaching the sliding disc. This feature contributes to retaining the specimen inside the tube as the latter is retracted.

Another manner of ensuring that the specimen is retained inside the tube is to provide the latter internally with retaining means, such as a projecting edge the lower part of which is oblique whereas the upper part is essentially perpendicular to the longitudinal axis of the tube. Internal barbs or the like are also conceivable.

Figure 6:
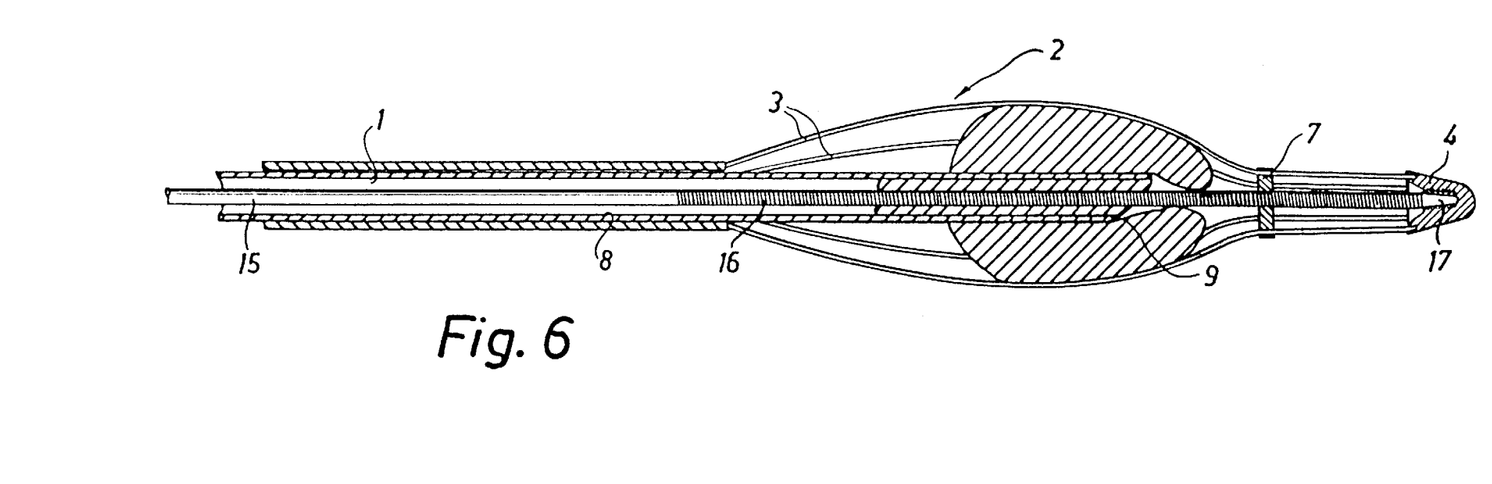
FIG. 6 is a view corresponding to FIG. 5 but shows another type of manipulating rod.

Alternatively, a second manipulating rod 15 is used instead to manipulate the sliding disc 7, as illustrated in FIG. 6. This second rod is formed with a tip 17 of sufficient length to allow the threads 16 of the rod to engage only the threads formed in the sliding disc and not the threads of the bottom member. When the tip 17 of the rod has reached the bottom member 4 it will exert an axial upwardly directed force on the sliding disc when turned further on the screw threads 16. Thus, the sliding disc 7 will be displaced towards the shank 1, whereby the basket with the specimen, such as an organ or tissue, therein will be shortened while at the same time the basket part positioned on the opposite side of the sliding disc will be maintained in a stretched and elongated state. The tip 17 of the rod makes it easier to force the rod through the specimen and in addition less friction is encountered when the tip while being rotated is pressed against the bottom member. Optionally, some kind of seat in the bottom member or the end part of the rod could be used to further reduce the rotation-induced friction.

As the sliding disc is being displaced, the specimen becomes immobilised inside the basket owing to radial forces directed from the elements of the basket towards the centre line, and in addition the specimen as such is compressed as is also the cavity forming inside the specimen as a cylindrical piece thereof is being cut out and is retracted together with the internal tube.

The cut out cylindrical pieces are stored inside the tube or, when the specimen is large, inside a container which is connected to the upper end of the tube. Alternatively, the specimen pieces may also be retrieved via the upper end of the tube as they are being collected inside the tube. Upon sufficient reduction of the specimen, allowing the basket containing the remaining portions of the specimen to pass through the outer sleeve, (the trocar), or if no trocar is used, through the abdominal wall, the basket is extracted from the patient.

Because the pressure exerted by the basket circumferentially around the specimen is comparatively even essentially concentric pieces of the original specimen will be extracted each time, whereby the previous positions of each extracted piece of the specimen may be established with a comparatively high degree of certainty. However, there is a certain risk in this case that during the extraction procedure the specimen turns while being compressed, for which reason the relative orientation of the extracted specimen pieces may be difficult to establish. In order to allow orientation of the pieces also under these circumstances it is possible, prior to the extraction, to mark one or several radii in the specimen, such as an organ or tissue. Likewise, the inner tube may be given such a peripheral configuration that it becomes possible to orientate the extracted cylindrical pieces. For instance, the inner tube may be formed with a slit or longitudinal ridge imparting an indication mark in the extracted pieces as well as in the remaining piece of the specimen.

Should histological examinations of the specimen not be necessary or not require reconstructibility, a cutting, helically shaped device or the like may replace the inner tube so as to fragmentize the specimen by drilling rather then by punching.

Figure 8:
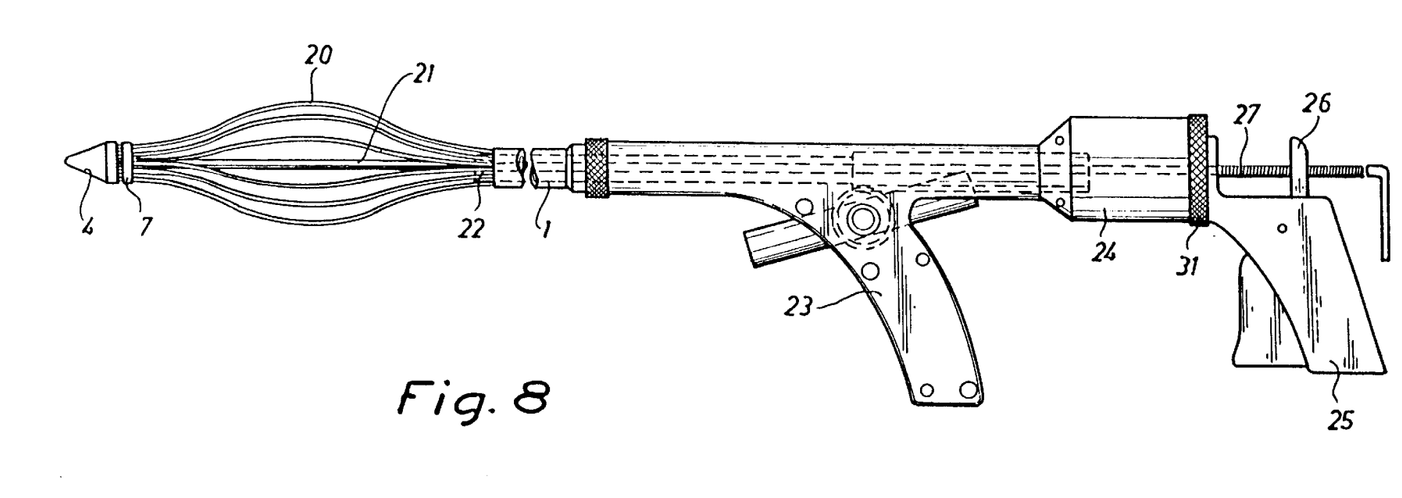
FIG. 8 shows a second embodiment of a device in accordance with the invention.

FIG. 8 illustrates a second alternative embodiment of the invention. In accordance with this embodiment the basket 20 has been given a pre-shaped, heavily bulging configuration by shaping the lengthwise extending wires of the basket in advance in such a manner that in their natural condition they exhibit an outwardly bulging arrow-like profile configuration. Consequently, the basket naturally will assume an at least partly expanded position. Contrary to the case in the first embodiment requiring an active pulling force in order to expand the basket, this second embodiment requires an active pushing force to compress the basket. In many contexts the pre-shaped basket is preferable because it more readily assumes the outwardly bulging position with consequential possibilities of entering the specimen, such as an organ or tissue, into the basket.

To compress the basket, allowing it to be inserted into the trocar, or to compress it after introduction of the specimen, a manipulating rod 21 is used in accordance with this embodiment which rod, when being pushed down through the shank part, exerts pressure on the bottom member 4, thus forcing said member 4 away from the shank part, whereby the basket 20 will be extracted longitudinally and be compressed laterally.

In accordance with this embodiment the shank part 1 has a grip member 23 whereby the device may be conveniently grasped during use. Inside the shank part extends, like in the previous embodiment, an inner tube 22 having a lower cutting edge. The opposite, upper end of the tube 22 debouches into a wider collection part 24 of the shank. The collection part preferably is formed with a removable close fitting lid 31 having closable end openings for passage-through of manipulating devices and the like.

On top of the collection part 24 is mounted a depressing means to force the manipulating rod downwards. The depressing means comprises a stationary arm 25 and a movable arm 26, the movable arm being arranged to engage in peripherally extending channels 27 formed in the upper end of the manipulating rod. In this manner the manipulating rod is forced down through the shank part when the arms 26, 27 of the depression means are forced together.

Alternatively, the shank part could be formed without the collection part and instead be equipped with a removable close-fitting lid with an aperture therein for passage-through of a manipulating rod and other required instruments, said lid being applied directly onto the shank part proper.

Preferably, the manipulating rod 22 has a threaded lower end (like the above-mentioned threaded manipulating rod 15), whereby upon rotation of the manipulating rod the sliding disc 7 will be displaced axially upwards or downwards owing to the thread engagement.

Figure 9:
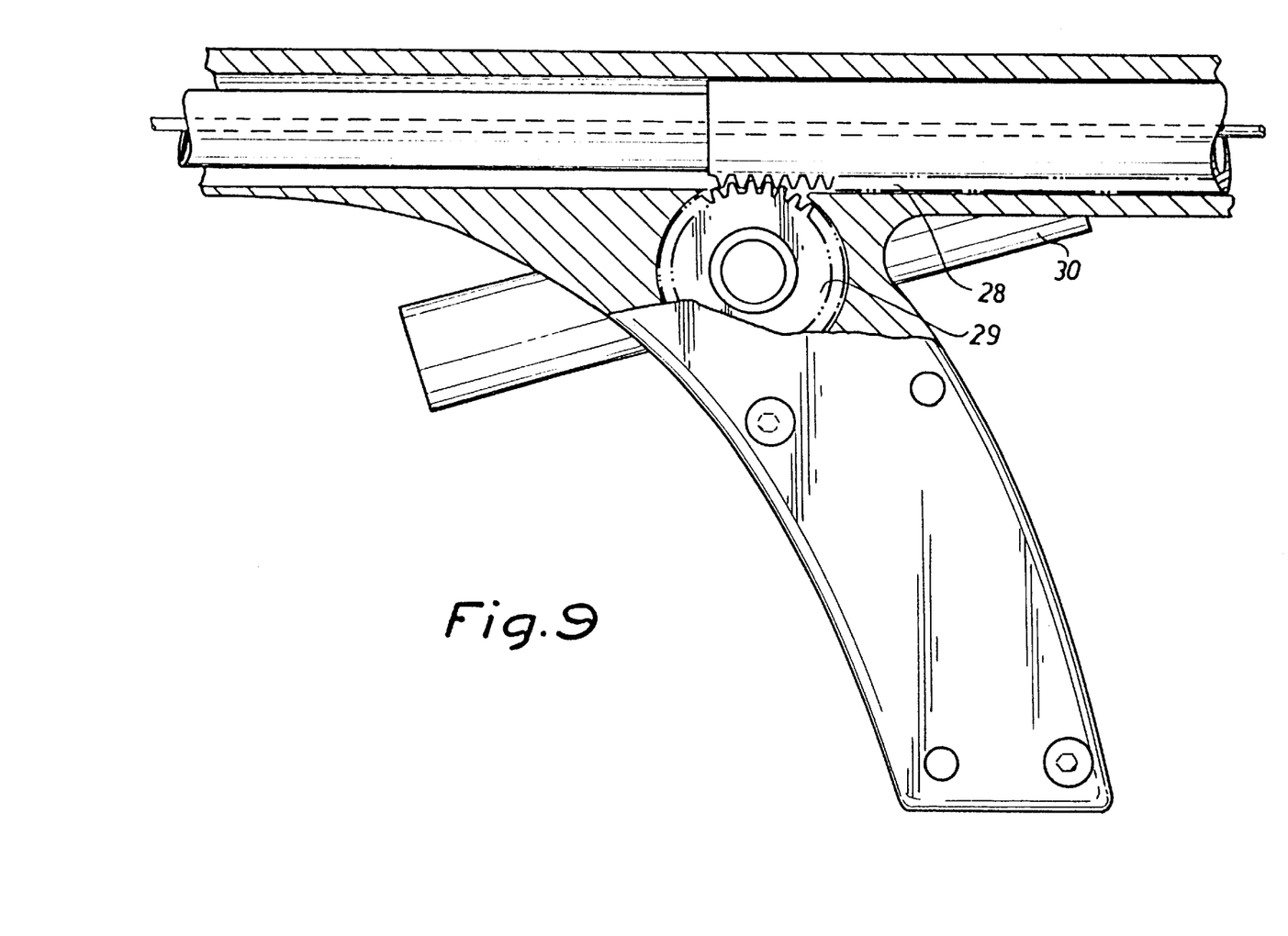
FIG. 9 is an enlarged view which partly in cross-section shows a part of the device of FIG. 8.

Preferably, as illustrated in FIG. 9, the inner tube is formed at least partly with teeth 28 allowing the tube to be conveniently displaced upwards or downwards axially by means of a sprocket wheel 29 which is rotatably mounted on the grip member and may be turned e.g. by means of a handle 30.

When the device in accordance with this embodiment is operated the basket is initially compressed or contracted to allow it to be inserted into and pushed down the trocar. The basket is then again allowed to expand and the specimen, such as an organ or tissue, is entered. Once the specimen is inside the basket the latter is again compressed, retaining the specimen in position, and the specimen is extracted in the same manner as in accordance with the first embodiment.

When the basket is being pushed down through the trocar the sliding a disc may optionally be pulled upwards to a position approximately at the middle of the basket to hold the latter in the compressed condition.

The flexible elements of the basket could vary as regards material, dimensions and number. A comparatively dense basket and a small specimen, such as an organ or tissue, form a satisfactory barrier between the surrounding organs and the cutting part of the tube, whereas a large specimen and a less dense basket give poorer protection.

Figure 11:
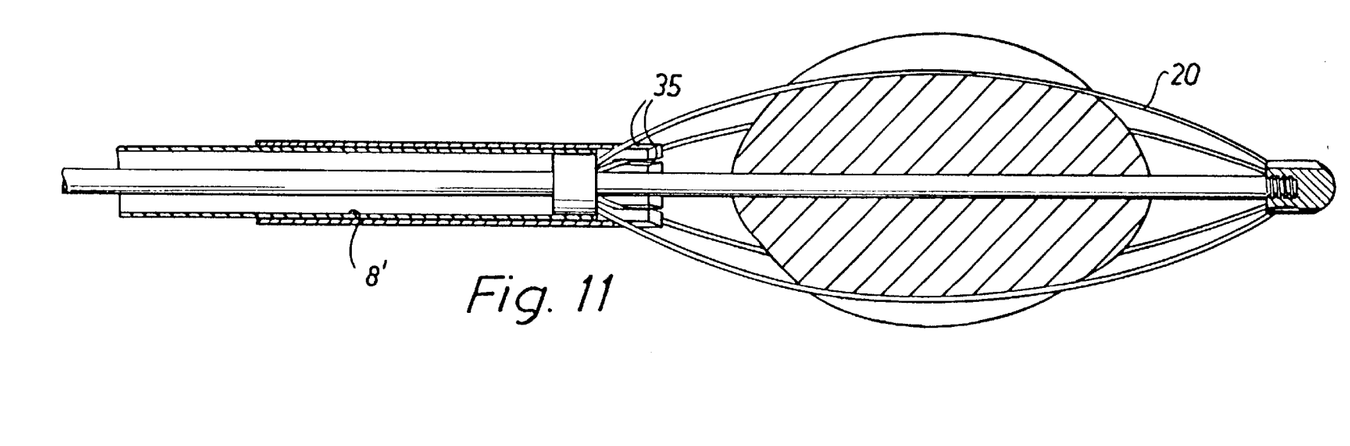
FIG. 11 shows a modified embodiment according to which the wires of the basket have a cutting function.

In accordance with an alternative embodiment illustrated in FIG. 11, the wires 20 of the basket have a cutting edge or similar means that faces the specimen, such as an organ or tissue, and the cutting tube 8' (the punch) is arranged on the shank exterior and in a manner corresponding to that described above it is movable upwards and downwards. When the cutting tube 8' is pushed downwards or when the basket is pulled into the tube, it will slide on the top of the basket wires, forcing the latter against the specimen. Owing to the cutting function of the wires the latter will cut into the specimen while at the same time the tube cuts out the cylindrical shape from the specimen retained inside the basket. In this manner the specimen will be divided into one central cylindrical piece and a number of segments. The cylinder piece will be extracted together with the instrument whereas the segments will fall into a cover (to be described in more detail further on) and be extracted individually, for instance by means of tongs. The number of segments corresponds to the number of wires 20 forming the basket. The cutting tube 8' may, when intended to be pushed downwards externally of the basket, preferably be formed with slits for reception therein of the basket wires 20. This arrangement stabilises the wires laterally. Obviously, other methods of providing this stabilising function on are possible.

Figure 14:
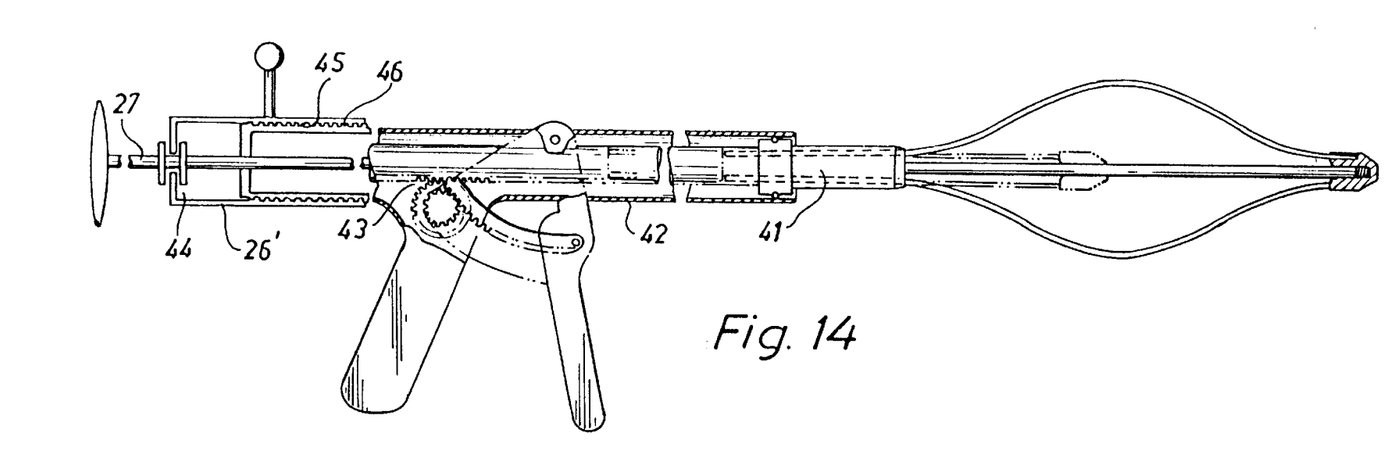
FIG. 14 is a modified embodiment according to which the basket is adapted for introduction through an outer sleeve.

As illustrated in FIG. 14 the basket preferably is arranged in accordance with this embodiment to completely or partly be displaceable through the external cutting tube 41 and into a protective sheath 42. Such displacement may be achieved for instance by means of the sprocket wheel arrangement discussed above including a handle to operate the inner punching means (see FIG. 9), acting through thread engagements on teeth 43 formed on the basket shank. The manipulating rod for displacement of the sliding means and for stretching the basket, the required lead-through arrangements and attachments for rotation of and power transfer to the manipulating rod in this case preferably are applied on the part of the shank projecting through the rear part of the gripping means. In addition, this embodiment allows for convenient variation of the functional length of the basket before the specimen is introduced therein, with consequential convenient adaptation to the size of the abdominal cavity.

In FIG. 14 dash and dot lines indicate a position, wherein the basket to a large extent has been pulled into the protective sheath.

FIG. 14 also illustrates an alternative embodiment of the depressing means. This means comprises a lid 26' having a rear abutment face in which a manipulating rod 27' is movably secured. The movable securement may be effected e.g. with the aid of two flanges 44 intended to be positioned on either side of the abutment face, in order to rotatably retain the manipulating rod to the lid. In addition, the lid is provided with internal threads 45 and matching external threads 46 are formed on the rear part of the protective sheath. In this manner the abutment face and accordingly also the manipulating rod may be displaced relatively to the sheath 43 and the basket upon turning of the lid.

Figure 12:
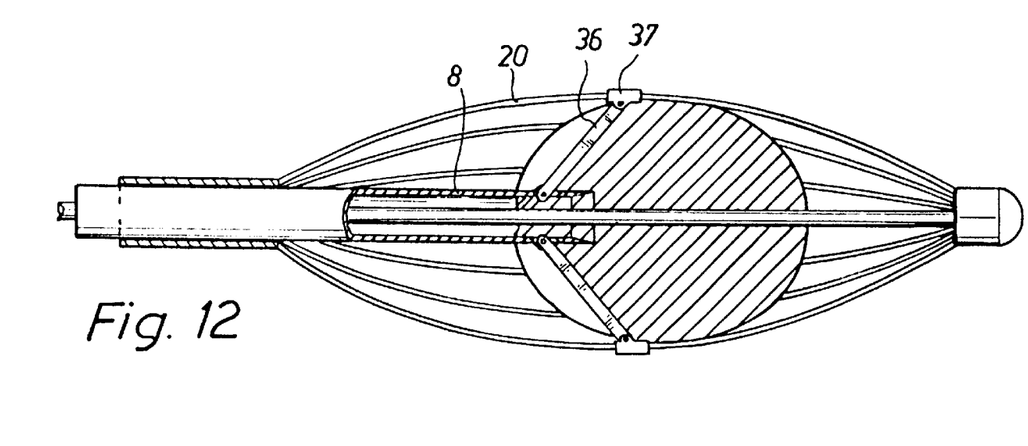
FIG. 12 is a further modified embodiment having cutting blades applied between the cutting tube and the basket.
Figure 13:
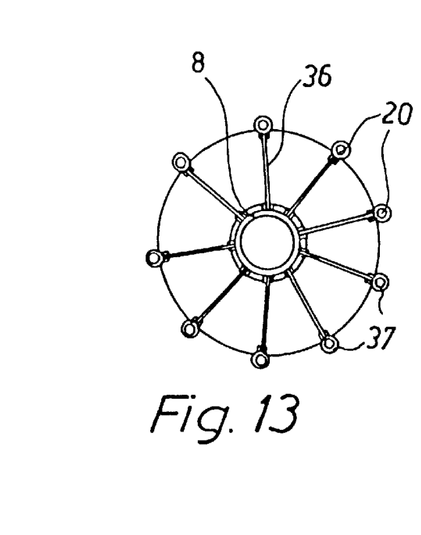
FIG. 13 is a cross-sectional view on line XIII—XIII through the device of FIG. 12.

In accordance with a further alternative embodiment illustrated in FIGS. 12 and 13, the punching means 8 may just like before be displaced inside the shank but be provided with cutting blades or wires 36 disposed between the distal end of the puncher 8, i.e. the end facing the specimen, and the basket wires 20. The blades 36 are attached for movement in the direction of the central longitudinal axis of the basket, e.g. by being attached to slides 37 moving along the basket wires. In this manner the blades will take part in the upwards and downwards movements of the punching means. When the punching means is forced down through a specimen, such as an organ of tissue, held inside the basket the central cylindrical piece of the specimen will be cut out as described with reference to the previous embodiments while at the same time the blades cut through the pieces of the specimen positioned externally of the punching means, dividing the specimen into segments. The number of such cutting blades could match that of the wires in the basket but other numbers obviously are possible.

Figure 15:
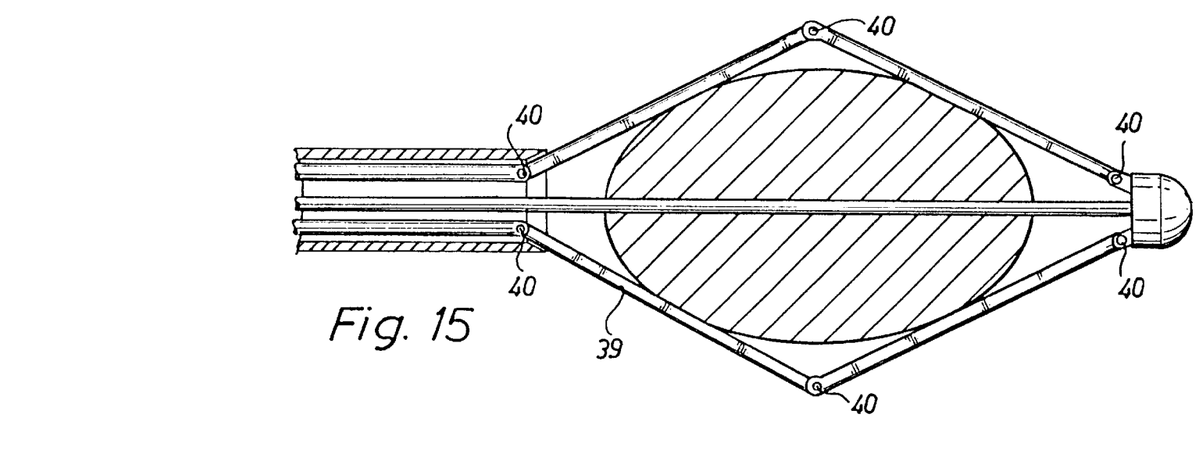
FIG. 15 is a modified embodiment wherein the basket consists of hingedly interconnected links.

FIG. 15 illustrates an alternative embodiment of a basket in accordance with the invention. Instead of wires 20 this basket has links 39 which preferably could be comparatively rigid but are hingedly attached to the shank and to the bottom Dart as well as to one another by means of pivots 40. In addition, the links preferably are formed with inwardly facing cutting edges. Preferably, the links are made from metal or some other material that is both resilient in the direction of the normal towards the broad side and could be given a cutting function directed against the specimen positioned inside the basket. The radially projecting broad sides of the links thus arranged provide radial stiffness and lateral flexibility. As a consequence, the links allow comparatively large specimen, such as an organ or tissue, to be introduced into the basket while at the same time the links are made to cut radially into the specimen when the outer punching means is depressed downwards on top of the basket links, the basket is culled into the gripping member via the outer punching means, and/or the basket is stretched by means of a manipulating rod secured to the bottom member in the manner described previously. As an alternative attachment means for attachment of the manipulating rod a plate or similar means could be used, which interconnects the links above the hinge mounting point in the shank. A basket thus configured divides the specimen, such as an organ or tissue, into one central cylindrical piece and a number of segments as described previously with respect to a basket formed with cutting wires.

In addition, the device in accordance with the invention may comprise exchangeable components, whereby a basket part, a shank part and so on may be easily disengaged from one another. In this manner it becomes possible to employ either the simple or the more complex functions of the instrument as also to vary the dimensions and the materials of the basket. In addition, discrete parts of the instrument could be checked and any worn-out components easily be replaced. In addition, cleaning and sterilisation are facilitated.

The devices in accordance with the embodiments recited above preferably are made mainly from metal, such as stainless steel or aluminium. However, more simple varieties made for instance from plastics to be discarded after use likewise are possible. Such simple varieties need not comprise a cutting inner tube if intended only to be used for smaller specimens, such as an organ or tissue, that need not be fragmentized before extraction but only require reshaping to the required fusiform shape necessary to allow the specimen to be extracted through the trocar. In the case of such smaller specimen it may be possible also to exclude the manipulating rod and the sliding disc, provided the basket has an advance configuration maintaining it in an expanded position. In this case the basket is compressed and is pushed down through the trocar, the specimen is positioned inside and shaped, whereupon the basket is pulled upwards again. To introduce the specimen into the basket, the openings existing between the basket wires in the expanded position might suffice but otherwise some mechanical instrument may be used to pull two wires apart. When the basket is extracted the trocar compresses the basket, since it has an inner diameter size which is smaller than the external diameter of the pre-shaped basket, and thus of the specimen contained therein. Because of the rotational symmetry of the basket the latter exerts a force on the specimen reshaping the latter into bobbin configuration, whereby extraction of the specimen through a trocar or other abdominal wall leadthrough passage is facilitated. However, it may be possible to equip the simplified device above with suction means or the like as described previously, allowing liquid and similar media to be sucked/squeezed out of the specimen, such as an organ or tissue. In this manner the volume of the specimen may be reduced, allowing also certain larger specimen to be extracted without first being fragmentized.

Figure 10:
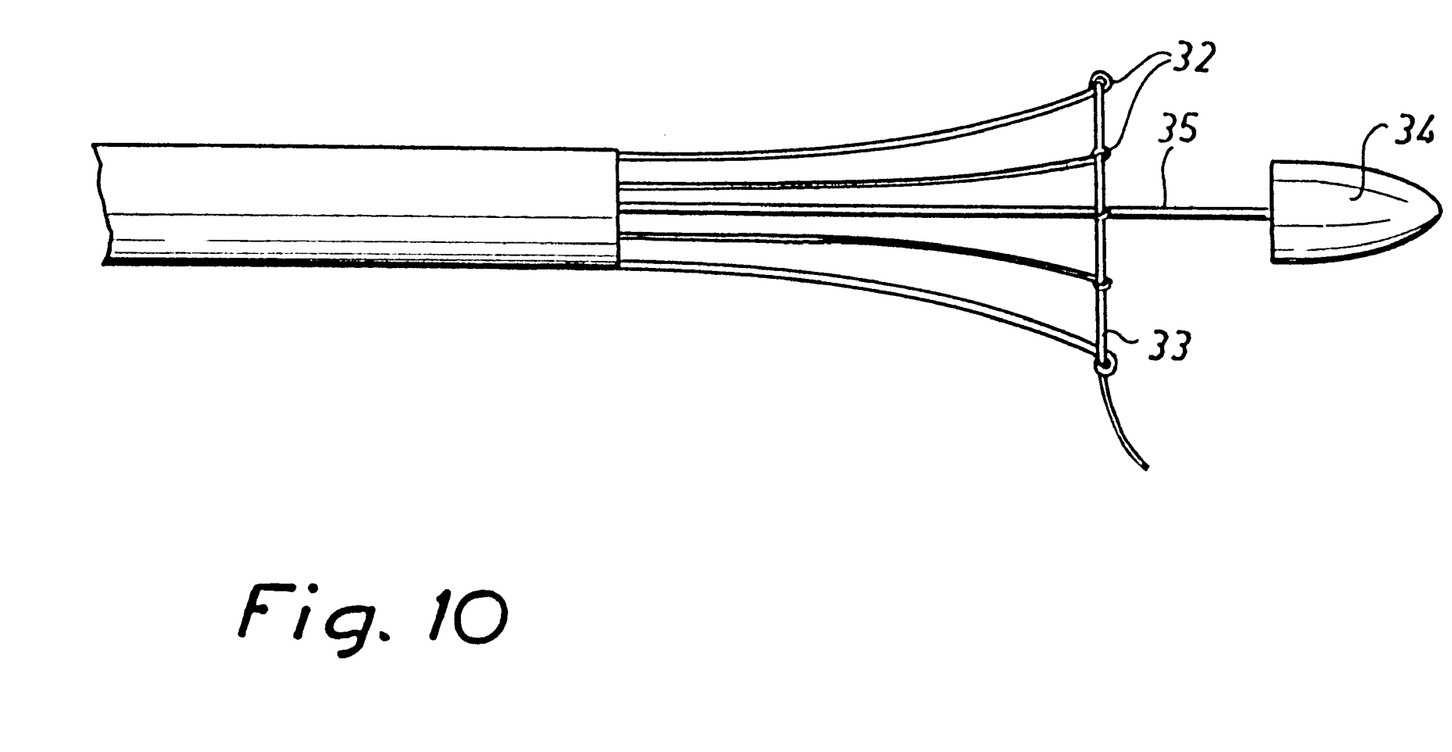
FIG. 10 illustrates a device in accordance with the invention having an opening at the distal end.

It is likewise possible to use a basket the distal end of which is formed with a closable opening as illustrated in FIG. 10. The closable opening may be produced e.g. by providing the wires at their lower ends facing away from the shank with small loops 32 or the like through which a pulling string 33 may extend, instead of the wire ends being attached to a bottom member. When the string length increases the opening expands whereas it is reduced when the string is pulled. Advantageously, the device is in this case equipped with a somewhat pointed bottom member 34 in order to make it easier to push the device thruogh the trocar. The bottom member 34 may for instance be mounted on a rod 35. In use, the rod 35 may be left in position when the specimen, such as an organ or tissue, is small. Otherwise the rod may be pulled back through the shank part together with the bottom member (in this case a bottom member preferably has an outer diameter size that is smaller than the inner diameter size of the shank). The string 33 may be pulled either by means of tongs or similar instruments inside the abdomen or be carried e.g. through the shank part, allowing it to be manipulated from the outside. It is likewise advantageous to arrange for the string to be secured in its opening closing position.

Figure 7:
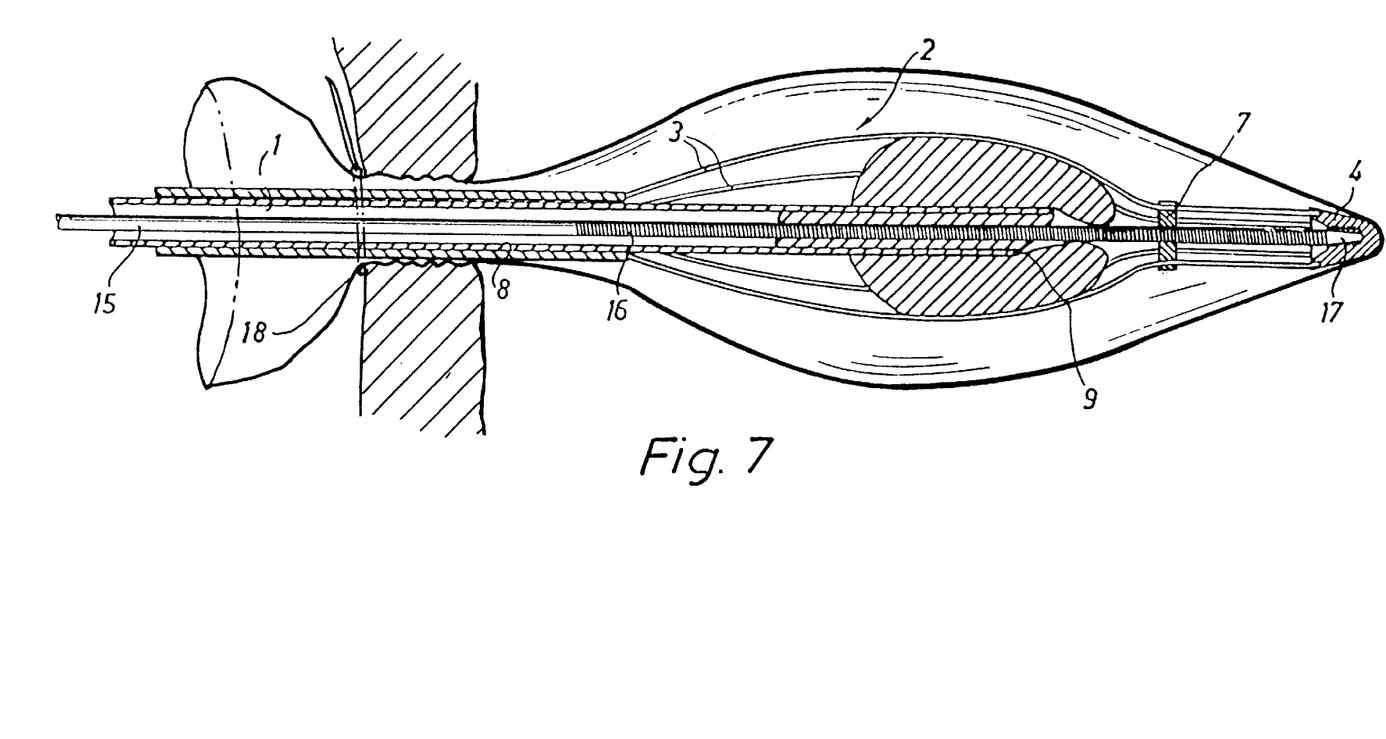
FIG. 7 shows the device of FIG. 6 and an outer protective cover.

When a specimen, such as an organ or tissue, contains infectious material or in cases of suspected cancer, there is a risk for harmful contamination of the abdominal cavity. As the specimen, such as an organ or tissue, is fragmentized and extracted the basket could in this case be provided with an external bag 18 as illustrated in FIG. 7, e.g. the commercially available bag "Endo Catch" supplied by Auto Sutur in USA. Alternatively, it is possible in order to provide a complete barrier between the basket with the contents therein and the surrounding abdominal cavity and the abdominal wall, to enclose the part of the instrument in contact with the patient completely in a cover, the instrument forming the body/carrier of the cover. Preferably, the cover is impermeable, transparent, inflatable and strong, and could for instance be made from polyurethane. In addition, it should be possible to close the cover to seal it from the part of the instrument situated outside the abdominal wall. The specimen, such an organ or tissue, is either entered through an opening in the cover before the instrument is inserted into the cover or after introduction of the instrument into the cover. In the first case the opening of the cover may be extracted through the abdominal wall before the instrument is inserted into the cover and after introduction of the instrument into the cover the opening of the cover is applied sealingly against the instrument to allow the cover to be inflated. In the second case a closable opening may be formed in the cover in the part thereof positioned inside the abdomen or the like. For instance, the opening may be formed by a closable zip or an end opening closable by a pull string. If in accordance with this latter variety the cover is fixedly attached to a basket having a distal end opening of the kind described above the basket will in principle serve as a cover stabilising reinforcement means.

In some situations it is essential that the cover is inflatable. This function provides for improved visibility and forms a protective barrier between the instrument including the specimen and surrounding organs inside the abdomen.

The cover could be of double-sheath type and be provided with an tubular channel extending to the intersheath space to subject said intermediate space to an overpressure or partial vacuum pressure, allowing the cover to be used to exert a pressure on the basket and the specimen contained therein for compressive purposes.

The above embodiment has been described with reference to the abdominal wall and cavity but relevant parts are applicable also to the thoracic wall and cavity as indeed any cavity in the body that may be considered for endoscopic surgery or to corresponding surgical situations where extraction of specimen causes a problem. For instance, the instrument may be used in abdominal surgery via the vagina. Obviously, a device in accordance with the invention may be also be used within veterinary surgery.

Several modifications of the invention, some of which have already been mentioned, are of course possible. As an example may be mentioned that the basket may be configured differently and instead of being formed from wires it could comprise an essentially covering wall having only one or a few openings therein. The basket wires could also have a different curvature. They could for instance be helically wound. When constructed from such wires the basket is caused to expand and contract by rotating the bottom member relatively to the shank part. Also, the basket may expand in other ways than by being compressed by means of a manipulating rod which is attached to the bottom member or by spring action as a result of advance shaping. The cutting inner tube or the manipulating rod could for example be equipped with expanding means which exert pressure from within against the basket in a radial direction. This effect could be achieved e.g. by pneumatic or mechanic means. The basket could also be made to expand by means of external instruments, i.e. instruments not connected to the device. It is likewise possible to arrange for the bottom member to be permanently attached instead of removably so in connection with trapping the specimen inside the basket. The bottom member could also be of a more simple construction, e.g including a simple gathering means or even be completely omitted. Several combinations of the various embodiments are of course also possible, and as example may be mentioned that the elongate elements of the basket may be formed by a combination of wires and links, the discrete element may be a wire, a link, or a combination of both, and an outer as well as an inner punching means may be used in the same embodiment. It is likewise possible to morcellate a specimen that is retained inside a basket in accordance with the invention by means of various varieties of cutting wires extending in or through the basket. Obviously, it is possible to adapt the device in accordance within the invention to automatic operation using a hydraulic, pneumatic or electric source of power. Such obvious modifications are encompassed by the invention as the latter is defined in the appended claims.

What is claimed is:

1. A device for use in endoscopic surgical operation to enclose, fix and extract a specimen from a cavity within a body, comprising:
    a shank part having a proximate end and a distal end,
    an entrapment part mounted on one end of said shank part,
    the entrapment part is provided with at least one expandable opening for insertion of the specimen,
    said opening expandable between an open condition and an at least partly closed condition,
    the entrapment part is changeable between a contracted position for insertion and extraction of the device into a cavity in the body, and an expanded condition for insertion of the specimen into the entrapment part,
    a manipulator is insertable through the shank part, thus causing the entrapment part to shift between its contracted position and expanded condition,
    said manipulator comprising a distal end formed to enable penetration of an entrapped specimen in the entrapment part.

2. A device as claimed in claim 1, wherein the entrapment part comprises elongate flexible elements and means for dividing the specimen in directions along the flexible elements.

3. A device as claimed in claim 2, wherein the flexible elements are connected to the shank part and are joined to a bottom member which is positioned essentially in a prolongation of a center axis of the shank part.

4. A device as claimed in claim 3, wherein each of the flexible elements have a cutting edge on which faces a center of the entrapment part.

5. A device as claimed in claim 1, wherein the entrapment part (2) is adapted to automatically, by a spring action, return from either the expanded condition or the contracted position.

6. A device as claimed in claim 1, wherein the manipulator has at least two active positions, one in which the entrapment part is expanded and one wherein a sliding disc, through which extend a peripheral parts of the entrapment part, is displaceable upwards and downwards along the entrapment part.

7. A device as claimed in claim 6, wherein the manipulator comprises at least one rod formed at least at a lower part with threads, and in that corresponding threads are formed in the sliding disc and/or a bottom member in which a lower part of the entrapment part is secured.

8. A device as claimed in claim 1 wherein the manipulator comprises at least one rod formed at least at a lower part with threads, and in that corresponding threads are formed in a sliding disc and/or a bottom member in which a lower part of the entrapment part is secured.

9. A device as claimed in claim 1, wherein the shank part comprises an inner sleeve, and the manipulator is at least partly displaceable inside said inner sleeve.

10. A device as claimed in claim 9, wherein said inner sleeve is provided with a lower cutting edge which faces the distal end of entrapment part.

11. A device as claimed in claim 1, wherein the shank part comprises an outer tube and a collection means which is displaceable into and out of said outer tube.

12. A device as claimed in claim 11, wherein the collection means is a second tube the outer diameter of which essentially equals or is slightly smaller than the interior diameter of an outer tube and the end of the second tube facing a distal end of the entrapment part is formed with a cutting edge that faces said entrapment part.

13. A device as claimed in claim 12, wherein the second tube is interconnected with the shank part by power transmission means to axially displace the second tube relative to the shank part and the entrapment part and to prevent inter-rotational movement between said shank part and said entrapment part.

14. A device as claimed in claim 1, wherein it further comprises an outer sheath which is formed by an elastic and at least partly transparent material, which is adapted to be passed over the entrapment part and at least parts of the shank and an end of said outer sheath which surrounds said entrapment part being one of closed or closable.

15. A device as claimed in claim 1, wherein the distal end of the manipulator has a pointed tip.

* * * * *